US006961615B2

(12) United States Patent
Kroll et al.

(10) Patent No.: US 6,961,615 B2
(45) Date of Patent: *Nov. 1, 2005

(54) SYSTEM AND METHOD FOR EVALUATING RISK OF MORTALITY DUE TO CONGESTIVE HEART FAILURE USING PHYSIOLOGIC SENSORS

(75) Inventors: Mark W. Kroll, Simi Valley, CA (US); Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 428 days.

This patent is subject to a terminal disclaimer.

(21) Appl. No.: 10/071,282

(22) Filed: Feb. 7, 2002

(65) Prior Publication Data

US 2003/0149453 A1 Aug. 7, 2003

(51) Int. Cl.[7] ............................................... A61N 1/18
(52) U.S. Cl. ........................................................ 607/18
(58) Field of Search ............................ 607/17, 18, 22, 607/24; 600/324–325

(56) References Cited

U.S. PATENT DOCUMENTS

| 4,712,555 A | 12/1987 | Thornander et al. | 128/419 PG |
| 4,788,980 A | 12/1988 | Mann et al. | 128/419 PG |

(Continued)

FOREIGN PATENT DOCUMENTS

WO  WO 01/23040 A1  4/2001  .......... A61N/1/365

OTHER PUBLICATIONS

Robbins, MD, et al., "Ventilatory and Heart Rate Responses to Exercise: Better Predictors of Heart Failure Mortality Than Peak Oxygen Consumption", Circulation, pp.: 2411–2416 (Dec. 14, 1999).

*Primary Examiner*—Mark Bockelman

(57) ABSTRACT

A congestive heart failure (CHF) mortality risk metric is automatically generated using an implantable medical device and, if it exceeds a predetermined threshold, a warning signal is issued indicating a significant risk of mortality due to CHF, perhaps necessitating more aggressive medical therapy. The CHF mortality risk metric is calculated based on a combination of estimated ventilatory response values and the slope of heart rate reserve as a function of predicted heart rates. Ventilatory response is estimated based on detected values of actual heart rate, arterial oxygen saturation, right ventricular $O_2$, stroke volume, tidal volume, and respiration rate. Heart rate reserve values are derived from the actual heart rate along with patient age and rest heart rate. The predicted heart rates, which represent the heart rates the patient would achieve if healthy, are derived from activity sensor signals. The CHF mortality risk metric is then calculated as a ratio of ventilatory response and the slope of the heart rate reserve. If the CHF mortality risk metric exceeds a critical threshold value, such as 90, the warning signal is generated. Also described herein are various techniques for estimating ventilatory response.

6 Claims, 4 Drawing Sheets

OTHER PUBLICATIONS

| | | |
|---|---|---|
| 4,802,481 A | 2/1989 | Schroeppel ........... 128/419 PG |
| 4,809,697 A | 3/1989 | Causey, III et al. ... 128/419 PT |
| 4,901,725 A | 2/1990 | Nappholz et al. ...... 128/419 PG |
| 4,940,052 A | 7/1990 | Mann et al. .......... 128/419 PG |
| 4,944,298 A | 7/1990 | Sholder ................ 128/419 PG |
| 4,944,299 A | 7/1990 | Silvian ................. 128/419 PG |
| 4,998,535 A | 3/1991 | Selker et al. ................ 128/696 |
| 5,267,564 A | 12/1993 | Barcel et al. ................ 128/634 |
| 5,300,093 A | 4/1994 | Koestner et al. .............. 607/32 |
| 5,466,254 A | 11/1995 | Helland ...................... 607/123 |
| 5,518,001 A | 5/1996 | Snell ........................ 128/697 |
| 5,573,550 A | 11/1996 | Zadeh et al. ................. 607/28 |
| 5,614,246 A | 3/1997 | Mund et al. ............... 427/2.24 |
| 5,685,315 A | 11/1997 | McClure et al. ............ 128/708 |
| 5,792,197 A | 8/1998 | Nappholz .................... 607/17 |
| 5,935,081 A | 8/1999 | Kadhiresan ................. 600/513 |
| 5,944,745 A | 8/1999 | Rueter ........................ 607/27 |
| 5,964,788 A | 10/1999 | Greenhut ..................... 607/17 |
| 5,974,340 A | 10/1999 | Kadhiresan ................... 607/18 |
| 5,980,463 A | 11/1999 | Brockway et al. .......... 600/485 |
| 6,021,351 A | 2/2000 | Kadhiresan et al. .......... 607/19 |
| 6,104,949 A | 8/2000 | Pitts Crick et al. ......... 600/547 |
| 6,135,970 A | 10/2000 | Kadhiresan et al. ........ 600/595 |
| 6,190,324 B1 | 2/2001 | Kieval et al. ............... 600/483 |
| 6,275,734 B1 | 8/2001 | McClure et al. .............. 607/27 |
| 6,336,903 B1 | 1/2002 | Bardy ........................ 600/508 |
| 6,438,408 B1 | 8/2002 | Mulligan et al. ............ 600/510 |
| 6,454,707 B1 | 9/2002 | Casscells, III et al. ..... 600/300 |
| 6,459,929 B1 | 10/2002 | Hopper et al. ............... 600/513 |
| 6,645,153 B2 * | 11/2003 | Kroll et al. ................. 600/481 |

\* cited by examiner

SYSTEM AND METHOD FOR EVALUATING RISK OF MORTALITY DUE TO CONGESTIVE HEART FAILURE USING PHYSIOLOGIC SENSORS

CROSS-REFERENCE TO RELATED APPLICATIONS

This application is related to commonly-assigned U.S. patent application Ser. No. 10/068,885, titled "System and Method for Evaluating Risk of Mortality Due to Congestive Heart Failure Using Physiologic Sensors," filed Nov. 11, 2003, now issued as U.S. Pat. No. 6,645,153.

FIELD OF THE INVENTION

The invention relates generally to an implantable cardiac stimulation device for the purpose of monitoring the progression of congestive heart failure or the efficacy of delivered heart failure therapies.

BACKGROUND OF THE INVENTION

Congestive heart failure (CHF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow become leaky, allowing regurgitation or back flow of blood. The impairment of arterial circulation deprives vital organs of oxygen and nutrients. Fatigue, weakness, and inability to carry out daily tasks may result. Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

CHF has been classified by the New York Heart Association (NYHA) into four classes of progressively worsening symptoms and exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations, or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of CHF are present even at rest and where increased discomfort is experienced with any physical activity.

Current standard treatment for heart failure is typically centered around medical treatment using angiotensin converting enzyme (ACE) inhibitors, diuretics, and digitalis. It has also been demonstrated that aerobic exercise may improve exercise tolerance, improve quality of life, and decrease symptoms. Heart transplantation is an option, but only in one out of every two hundred cases. Other cardiac surgery may also be indicated, but only for a small percentage of patients with particular etiologies. Although advances in pharmacological therapy have significantly improved the survival rate and quality of life of patients, patients in NYHA Classes III or IV, who are still refractory to drug therapy, have a poor prognosis and limited exercise tolerance. Cardiac pacing has been proposed as a new primary treatment for patients with drug-refractory CHF.

By tracking the progression or regression of CHF more closely, treatments can be administered more effectively. Commonly, patients adapt their lifestyle and activities to their physical condition. The activity level of the patients with NYHA Class III or IV would be much lower than that of the patients with NYHA Class I or II. The change in lifestyle or activity level, due to the patient's heart condition, will be reflected by activity and respiration physiological parameters.

Besides various assessments of the cardiac function itself, assessment of activity and respiration are typically performed. This includes maximal exercise testing in which the heart rate and maximum ventilation are measured during peak exertion. However, peak exercise performance has been found to not always correlate well with improvements in a patient's clinical condition. Therefore, sub-maximal exercise testing can also be performed, such as a six-minute walk test. While improvements in sub-maximal exercise may suggest an improvement in clinical condition, sub-maximal exercise performance can be variable in that it is dependent on how the patient happens to be feeling on the particular day of the test.

To obtain a more general assessment of the patient's activity on a daily basis, patients are often asked to answer questionnaires regarding numerous aspects of daily life. Such questionnaires are inherently subjective. Nevertheless, collected information is useful to the physician. Since existing CHF treatments are palliative and not curative, a major goal in administering therapies is to improve the quality of daily life which is directly reflected by the level and variety of activities the patient is comfortable performing.

Thus, it would be desirable to have an objective means of chronically and non-invasively monitoring physiological parameters indicative of a patient's overall well-being on an ongoing, daily basis. This would enhance the physician's ability to optimize and carefully tailor therapies for stabilizing CHF.

A number of attempts have been made previously to provide for chronic monitoring of physiological parameters associated with CHF using implantable cardiac devices, such as pacemakers, in conjunction with physiological sensors. Reference is made to U.S. Pat. No. 5,518,001 to Snell; U.S. Pat. No. 5,944,745 to Rueter; U.S. Pat. No. 5,974,340 to Kadhiresan; U.S. Pat. No. 5,935,081 to Kadhiresan; U.S. Pat. No. 6,021,351 to Kadhiresan et al.; and U.S. Pat. No. 5,792,197 to Nappholz. Reference is also made to U.S. Pat. No. 4,901,725 to Nappholz, et al.; and U.S. Pat. No. 5,964,788 to Greenhut, that generally describe rate-responsive pacemakers using impedance measurements of respiration for controlling the pacing rate.

U.S. patent application Ser. No. 09/746,235, entitled "System and Method for Monitoring Progression of Cardiac Disease State Using Physiologic Sensors," filed Dec. 21, 2000, describes a technique for monitoring physiological parameters associated with the progression, stabilization, or regression of symptoms of heart disease such as congestive heart failure (CHF). The monitoring is implemented by ongoing surrogate measurement of standard and direct measurements, such as daily activity and respiratory and cardiac rate response, utilizing existing implantable, rate-responsive stimulation devices that incorporate activity, respiration, and/or other sensors. The system includes a sensor that measures activity and/or minute ventilation when triggered by changes in the sensed intrinsic heart rate and/or changes in a sensor-indicated pacing rate. The system processes and displays the measured activity or minute ventilation data to interpolate diagnostic relationships between activity, minute ventilation, heart rate, or sensor-indicated pacing rate, that are representative of the overall well-being of the patient, thus reflective of the severity of CHF symptoms. Activity and minute ventilation data collected upon each heart rate or sensor-indicated pacing rate change are stored in histogram bins assigned to defined heart rate or sensor-indicated pacing rate ranges. After a predetermined period of data collection, the data for each rate range is averaged and statistical or mathematical analysis is performed to determine correlation or regression coefficients that define the relationships between activity, heart rate, sensor-indicated pacing rate, or minute ventilation. A graphical display of the stored averages and the relationship coefficients may be provided for analysis. U.S. patent application Ser. No. 09/746,235 is incorporated herein by reference in its entirety.

Although the techniques of U.S. patent application Ser. No. 09/746,235 help fulfill the need for a method of chronically and objectively monitoring related physiological indicators of the severity of CHF to thereby reflect a worsening or improving condition associated with therapy delivery, room for improvement remains. In particular, it would be desirable to provide a technique for more directly and effectively measuring the severity of CHF based on measurements of heart rate, arterial oxygen saturation, right ventricular $O_2$, stroke volume, tidal volume, respiration rate, etc. and, in particular, for providing a technique for generating a warning signal to the patient or physician if the risk of mortality exceeds a critical threshold. It is to these ends that aspects of the present invention are primarily directed.

In this regard, recent studies have suggested that ventilatory response to exercise (i.e. minute ventilation divided $CO_2$ volume at peak exercise) and chronotropic index (i.e. heart rate reserve as a function of exercise) may be effective predictors of the severity of CHF. See "Ventilatory and Heart Rate Responses to Exercise: Better Predictors of Heart Failure Mortality Then Peak Oxygen Consumption", Robbins et al., *Circulation*, Dec. 14, 1999. Accordingly, aspects of the invention are also directed to generating a combined CHF metric based both on estimates of the ventilatory response to exercise and chronotropic index. Other aspects are directed to techniques for estimating the ventilatory response to exercise using various measurement proxies, particularly surrogates for a direct measurement of $CO_2$ volume.

SUMMARY OF THE INVENTION

In accordance with a first aspect of the invention, a method is provided for determining a risk of mortality to CHF using an implantable medical device having a plurality of sensors and a control unit for processing signals received from the sensors. Based on information received from the sensors, the control unit determines a value representative of a risk of mortality to CHF for the patient, then compares the value with a threshold value and generates a warning signal if the risk of mortality exceeds the threshold value. In this manner, if the severity of CHF increases to the point that it exceeds a critical threshold, the warning signal is generated to thereby advise the patient or physician to take appropriate steps such as initiating more aggressive medical therapy.

The risk of risk of mortality to CHF for the patient may be determined based either on ventilatory response to exercise of the patient or heart rate reserve as a function of exercise for the patient. The control unit then generates a single CHF risk metric based on both ventilatory response and heart rate reserve as a function of exercise. Both the ventilatory response of the patient and the heart rate reserve as a function of exercise for the patient may be determined at sub-maximal exertion levels. Thus, it is not necessary for the patient to exercise at a maximum level to determine the CHF risk metric.

In an exemplary embodiment, ventilatory response is estimated based on heart rate, arterial oxygen saturation, right ventricular $O_2$, stroke volume, tidal volume, and respiration rate detected at sub-maximal exertion levels. Heart rate reserve as a function of exercise is estimated by measuring actual patient heart rates at various sub-maximal levels of exertion, determining heart rate reserve at the various sub-maximal levels of exertion based on the actual heart rates and then predicting the heart rate the patient would achieve if healthy at various levels of exertion. The CHF metric is then calculated by dividing time-averaged ventilatory response values at the various sub-maximal levels of exertion by the slope of heart rate reserve as a function of predicted heart rate.

In accordance with a second aspect of the invention, various methods for estimating ventilatory response are provided. In one method, ventilatory response is estimated by receiving signals representative of heart rate, arterial oxygen saturation, right ventricular $O_2$, stroke volume, tidal volume, respiration rate and then calculating:

$$VR = (\text{Tidal Volume} \times \text{Respiratory Rate}) / (1.14 \times (\text{Arterial } O_2 - \text{Right ventricular } O2) \times (\text{Heart Rate}) \times (\text{Stroke Volume})).$$

In another method, ventilatory response is estimated by multiplying the ventilation amplitude by the ventilation rate (used as a proxy for respiration response) and correlating with the sinus rate. As yet another alternative, since $CO_2$ production is correlated with most activity, activity sensors are used as a surrogate for determining $CO_2$ production. With this latter technique, a minute ventilation sensor value is divided by an activity sensor value (scaled appropriately) and then correlated with sinus rate to yield an estimate of VR.

Thus various techniques are provided for estimating ventilatory response using an implantable medical device and for automatically evaluating risk of mortality due to CHF also using the implantable medical device. Other objects, features and advantages of the invention will be apparent from the detailed description to follow.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

Figure 1:
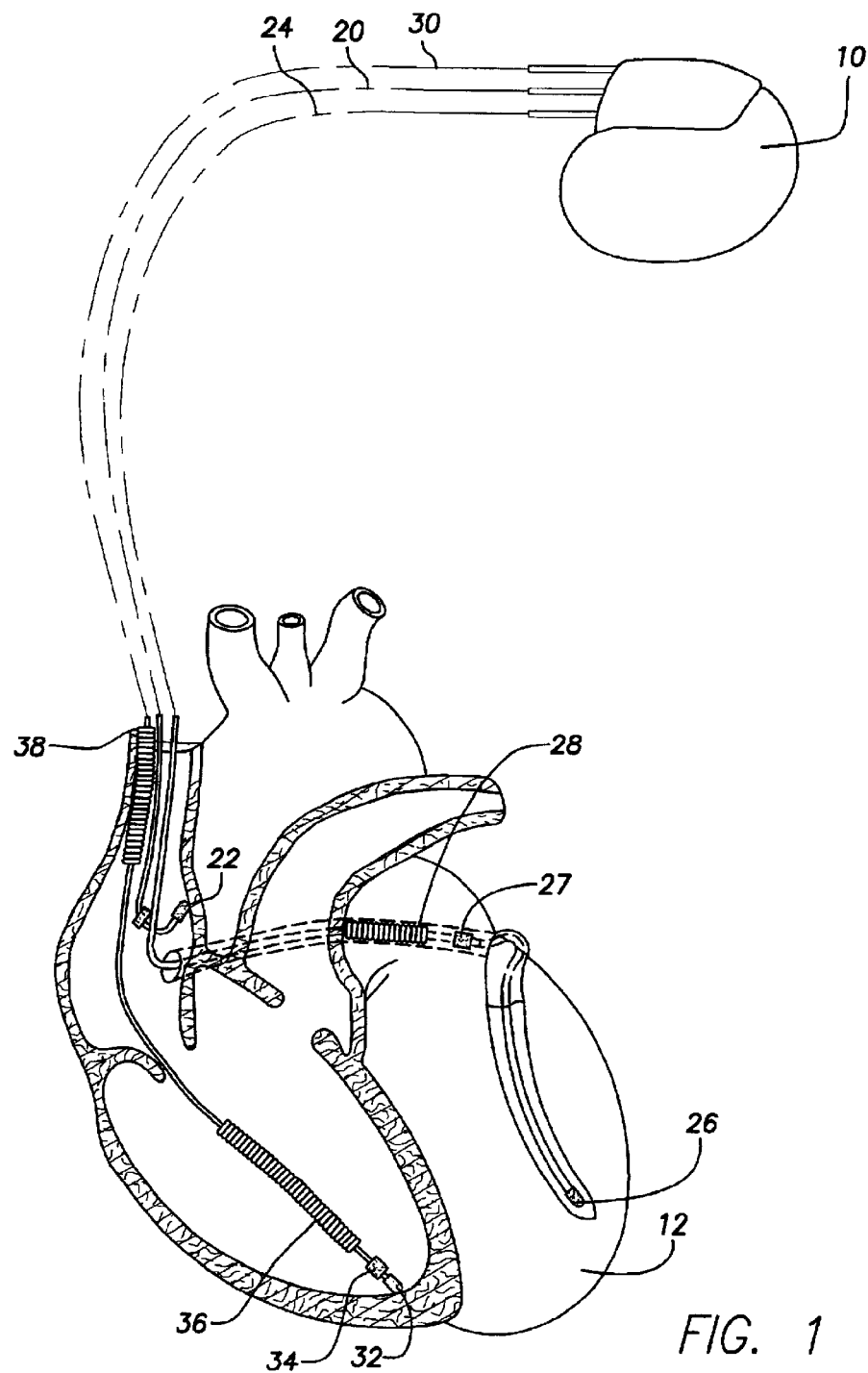
FIG. 1 is a simplified, partly cutaway view illustrating an implantable stimulation device in electrical communication with at least three leads implanted into a patient's heart for delivering multi-chamber stimulation and shock therapy.

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.
Stimulation Device FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, refer to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, entitled "Coronary Sinus Lead with Atrial Sensing Capability" (Helland), which patent application and patent, respectively, are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
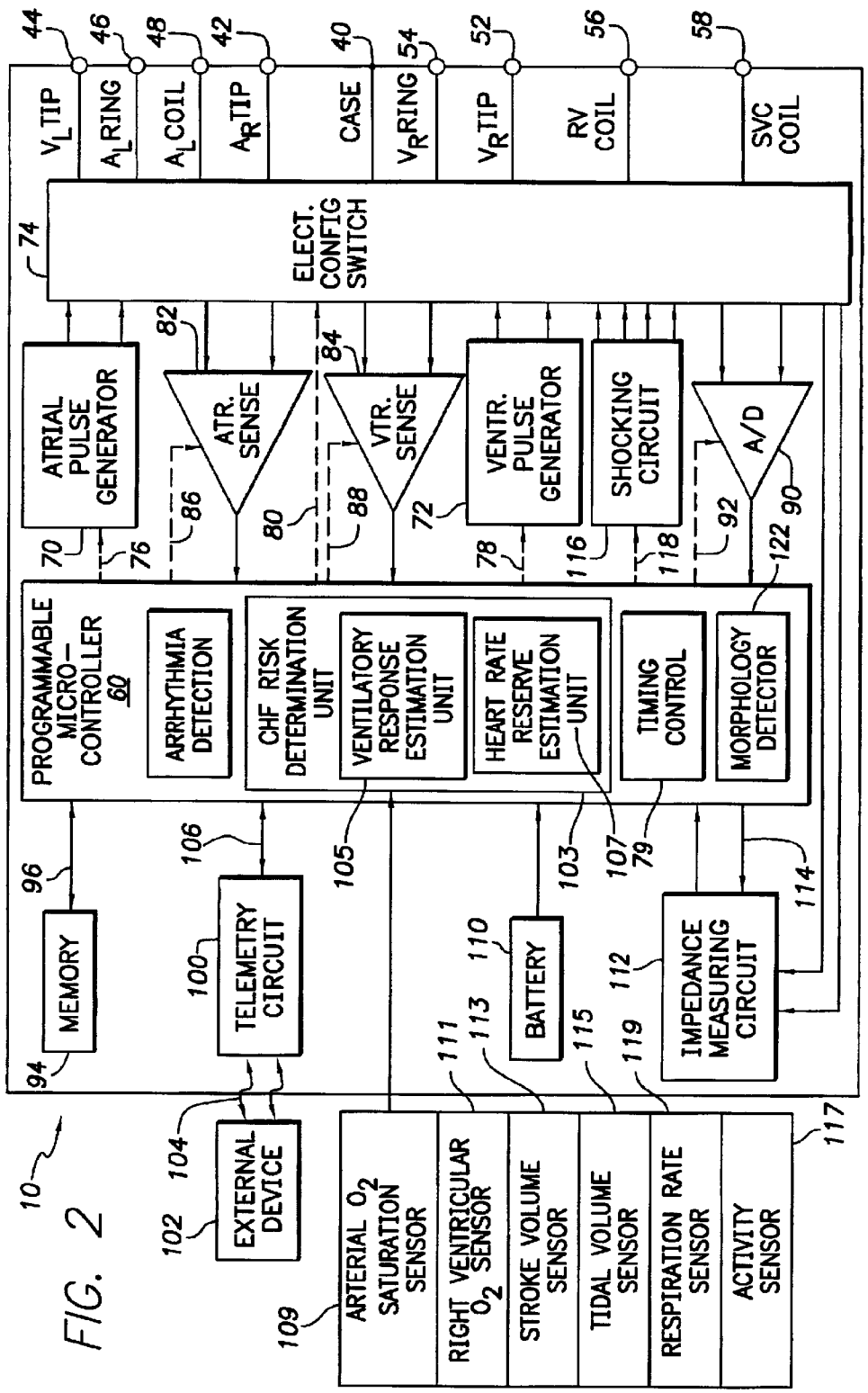
FIG. 2 is a functional block diagram of the multi-chamber implantable stimulation device of FIG. 1, illustrating the basic elements that provide cardioversion, defibrillation and/or pacing stimulation in four chambers of the heart and particularly illustrating a CHF risk determination unit for automatically evaluating the risk or mortality to CHF within the patient based on values received from various physiological sensors.

FIG. 2 illustrates a simplified block diagram of the multi-chamber implantable stimulation device 10 which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber (s) with cardioversion, defibrillation and/or pacing stimulation.

The stimulation device 10 includes a housing 40 which is often referred to as a "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the right atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial ring electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry or processor, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

Representative types of control circuitry that may be used with the present invention include the microprocessor-based control system of U.S. Pat. No. 4,940,052 (Mann et al.), and the state-machines of U.S. Pat. No. 4,712,555 (Thornander et al.) and U.S. Pat. No. 4,944,298 (Sholder). For a more detailed description of the various timing intervals used within the stimulation device and their inter-relationship, refer to U.S. Pat. No. 4,788,980 (Mann et al.). These patents (U.S. Pat. Nos. 4,940,052; 4,712,555; 4,944,298; and 4,788,980) are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, ventricular interconduction (V—V) delay, pacing mode, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the sensing circuits, 82 and 84, preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

For a more complete description of a typical sensing circuit, refer to U.S. Pat. No. 5,573,550, entitled "Implantable Stimulation Device Having a Low Noise, Low Power, Precision Amplifier for Amplifying Cardiac Signals" (Zadeh et al.). For a more complete description of an automatic gain control system, refer to U.S. Pat. No. 5,685,315, entitled "Cardiac Arrhythmia Detection System for an Implantable Stimulation Device" (McClure et al.). These patents (U.S. Pat. No. 5,573,550; and U.S. Pat. No. 5,685,315) are hereby incorporated herein by reference.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, where the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 12 within each respective tier of therapy. A feature of the stimulation device 10 is the ability to sense and store a relatively large amount of data (e.g., from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104. For examples of such devices, refer to U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), all of which are hereby incorporated herein by reference.

In a preferred embodiment, the stimulation device 10 further includes a set of physiologic sensors for detecting various physiological parameters of the patient. More specifically, the following sensors are shown: an arterial oxygen saturation sensor 109, a right ventricular $O_2$ sensor 111, a stroke volume sensor 113, a tidal volume sensor 115, a respiration rate sensor 119 and an activity sensor 117.

A CHF risk determination unit 103 of the microcontroller inputs signals from various physiological sensors and automatically determines a CHF metric representative of the risk of mortality to CHF. The CHF metric is compared with a predetermined threshold value stored in memory 94, and if it exceeds the threshold values, a warning signal is generated. The various sensors and the operation of the CHF risk determination unit are described in detail below. Note that, although the sensors are all shown as being external to the housing of the stimulation device, some of the sensors may instead be mounted therein. The CHF risk determination unit includes a ventilatory response estimation unit 105 and a heart rate reserve estimation unit 107, which generate values from which the CHF metric is derived.

In addition to aiding in the evaluation of the risk of mortality to CHF, the aforementioned activity sensor or other appropriate sensors may also be employed as a "rate-responsive" sensor for using adjusting pacing stimulation rate according to the exercise state of the patient. Accordingly, microcontroller 60 responds by adjusting the various pacing parameters (such as rate, AV Delay, V—V Delay, etc.) which control how and when the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 via a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11–40 joules) energy, as controlled by the microcontroller 60. Such shocking pulses are applied to the patient's heart through at least two shocking electrodes, as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (e.g., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of 5–40 joules), delivered asynchronously (since R-waves may be too disorganized) and pertaining exclusively to the treatment of fibrillation. Accordingly, the microcontroller 60 is capable of controlling the synchronous or asynchronous delivery of the shocking pulses.

Determination of Risk of Congestive Heart Failure

Figure 3:
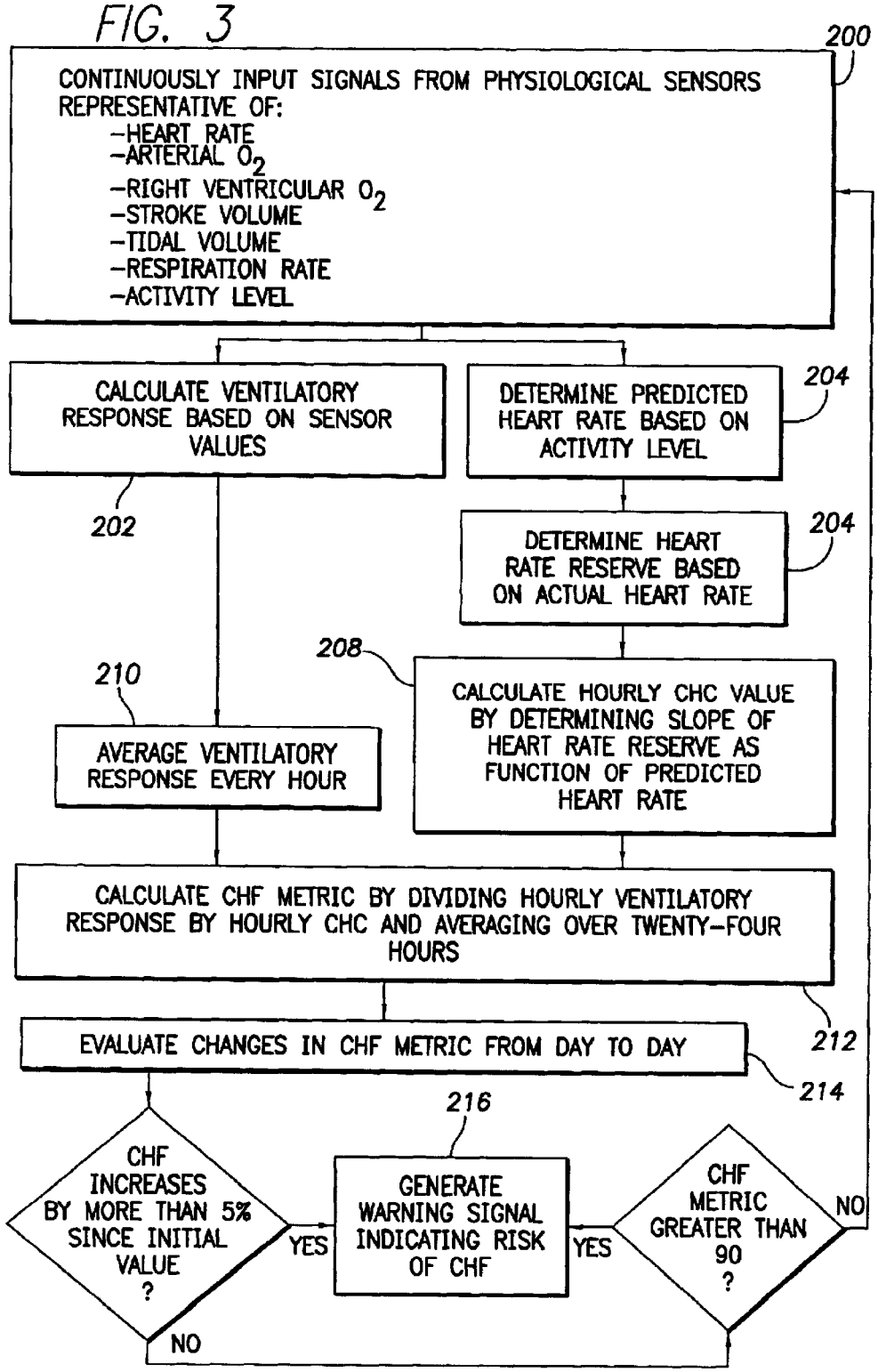
FIG. 3 is a flow diagram illustrating a method performed by the CHF risk determination unit of FIG. 2.

In FIG. 3, a flow chart is shown describing an overview of the operation and features implemented in one embodiment of the stimulation device 10. In this flow chart and the other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device.

The method of FIG. 3 is employed for patients with an intact sinus node. Initially, at step 200, the CHF risk determination unit (103) begins to continuously input signals from various physiological sensors: specifically an arterial oxygen saturation sensor, a right ventricular $O_2$ sensor, a stroke volume sensor, a tidal volume sensor, a respiration rate sensor and an activity sensor. The CHF risk determination unit also inputs the current heart rate as detected by the pacemaker itself. Note that many of the physiological sensors may need to be calibrated prior to activation of the CHF risk determination unit. Calibration is performed in accordance with conventional techniques. For some of physiological sensors, calibration involves the use of a stress test performed while the patient visits the physician. In particular, proper calibration of the activity sensor may require a stress test. The method of FIG. 3 assumes that all sensors are properly calibrated.

At step 202, the ventilatory response estimation unit of the CHF risk determination unit calculates the current ventilatory response (VR) based upon the signals from the various sensors. VR is calculated by first determining the minute ventilation (i.e. $V_E$) and $VCO_2$ then dividing $V_E$ by $VCO_2$ at the current exertion level.

$$VR = V_E/VCO_2. \quad \text{Eq. 1}$$

VR is ordinarily determined only at peak exercise. However, it has been found that VR is an effective predictor of CHF even at other exertion levels. Hence, VR can be determined at any exertion level for the purposes of evaluating the risk of mortality of the patient. Further details regarding this technique and other techniques for determining VR are provided below.

Simultaneously, at step 204, the heart rate reserve estimation unit of the CHF risk determination unit determines the predicted heart rate of the patient based on activity sensor values in accordance with conventional techniques. The predicted heart rate may differ from the actual heart of the patient. Indeed, in patients suffering CHF, the predicted heart rate is often considerably higher than the actual heart rate, particularly at high exertion levels. At step 206, the CHF risk determination unit calculates a heart rate reserve (HRR) value based on the actual heart rate. Details of the manner by which HRR is calculated are provided below with respect to FIG. 4. The HRR values are stored along with the corresponding predicted heart rate. Every hour, at step 208, the slope of HRR as a function of predicted heart rate is calculated based on the HRR values detected over the previous hour and stored. This slope is referred to herein as the ChC value. Details of the manner by which ChC is calculated are also provided below with respect to FIG. 4. Also, every hour, the VR values detected over the previous hour are averaged and stored, at step 210.

Once the hourly ChC and VR values have been determined, the CHF risk determination unit generates and stores an hourly CHF metric at step 212 by calculating the ratio of the latest VR value to the latest ChC value:

$$CHF\ metric = VR/ChC. \quad \text{Eq. 2}$$

Then, once per day, the CHF risk determination unit averages the CHF metric values detected over the last twenty-four hours and compares the latest averaged CHF metric with previously averaged CHF metrics, at step 214. If the CHF metric increases by more than 5% over a stored baseline metric (typically the first CHF metric calculated and stored after initial calibration of the sensors), a warning signal is generated at step 216 indicative of an increased risk of mortality due to CHF. The warning signal is also generated if the CHF metric exceeds a pre-stored threshold value of 90. Depending upon the configuration of the pacemaker, the warning signal is generated by causing the pacemaker to periodically vibrate inside the patient. Alternatively, the pacemaker may transmit an electronic warning signal to an external device, which displays the warning for the patient or forwards the warning to the patient's physician. As yet another alternative, a warning indicator may simply be stored within the pacemaker for subsequent transmission to an external programmer during a subsequent follow-up session between the patient and physician.

In any case, by automatically generating the CHF metric based on both VR and ChC and by providing a warning signal based on the CHF metric, the patient and/or physician are notified of the increased risk of mortality and appropriate steps can be taken, such as providing for aggressive therapies or regimes of different medications. The CHF metric is preferably determined based on both VR and ChC to provide the best assessment of risk of CHF. In the alternative, though, risk assessment may be based on either on just VR or just ChC. If VR only is used, the VR value calculated at step 210 is averaged every twenty-four hours and compared with a predetermined VR-based risk threshold value set to 45. If VR falls below 45, there is a significant risk of mortality and the warning signal is generated. If ChC only is used, the ChC value calculated at step 208 is averaged every twenty-four hours and compared with a predetermined ChC risk threshold value set to 0.5. If ChC falls below 0.5, the warning signal is generated. Note that if the patient does not have an intact sinus node, only VR is determined and hence the warning signal is generated based solely on VR.

Insofar as the determination VR is concerned, a number of techniques may be employed. In the first, oxygen saturation is used to estimate carbon dioxide production for the purposes of estimating VR, wherein VR:

$$VR = (\text{Tidal Volume} \times \text{Respiration Rate})/VCO_2. \quad \text{Eq. 3}$$

As noted, VR is ordinarily determined only at peak exercise. However, it has been found that VR is an effective predictor of CHF even at other exertion levels. $VCO_2$ is set equal to the respiratory exchange ratio ($\alpha$) times $VO_2$. Although, strictly speaking, the respiratory exchange ratio a varies slightly according to the level of activity of the patient, $\alpha$ can be reliably approximated by 1.14 for patients with CHF. Hence, $CO_2 = \alpha VO_2$.

Meanwhile, $VO_2$ is determined as follows:

$$VO_2 = (\text{Arterial } O_2 \text{ Saturation} - \text{Right Ventricular } O2) \times (\text{Heart Rate}) \times (\text{Stroke Volume}) \quad \text{Eq. 4}$$

Hence, $$VR = (\text{Tidal Volume} \times \text{Respiratory Rate})/(\alpha \times (\text{Arterial } O_2 - \text{Right Ventricular } O_2) \times (\text{Heart Rate}) \times (\text{Stroke Volume})). \quad \text{Eq. 5}$$

Thus, VR can be approximated based on the patients heart rate and on values derived from the arterial oxygen saturation sensor, Right Ventricular $O_2$ sensor, stroke volume sensor, tidal volume sensor, and respiration rate sensor. An arterial oxygen saturation sensor is described in U.S. Pat. No. 5,267,564 entitled "Pacemaker Lead For Sensing A Physiologic Parameter of the Body" to Barcel, et al. A right ventricular $O_2$ sensor is described in U.S. Pat. No. 5,614,246 to Mund et al.

A stroke volume sensor is described in U.S. Pat. No. 4,802,481 entitled "Apparatus For Controlling Pacing Of A Heart In Response To Changes In Stroke Volume" to Schroeppel. A tidal volume sensor is described in U.S. Pat. No. 5,980,463 entitled "Method for Respiratory Tidal Volume Measurement" to Brockway et al. A respiration rate sensor is described in U.S. Pat. No. 5,300,093 entitled "Apparatus And Method For Measuring, Formatting and Transmitting Combined Intracardiac Impedance Data And Electrograms" to Koestner et al. Alternatively, rather than separately sensing Tidal Volume and Respiratory Rate and multiplying these values together to yield minute ventilation, a minute ventilation sensor can instead by used to directly detect minute ventilation. An appropriate minute volume sensor is described in the aforementioned U.S. Pat. No. 4,901,725 entitled "Minute Volume Rate-Responsive Pacemaker" to Nappholz, et al. Each of these patents is incorporated by reference herein.

If no stroke volume sensor is employed, VR can be further approximated by setting the stroke volume to a predetermined constant value of, for example, about 50 ml for a CHF patient. Likewise, if no arterial $O_2$ sensor is employed, VR can be further approximated by setting arterial $O_2$ to a predetermined value of, for example, 0.95. If the patient does not have an intact sinus node, the sensor indicated rate derived from the activity sensor is used in Eq. 5.

VR can also be determined by multiplying the ventilation amplitude by the ventilation rate (used as a proxy for respiration response) and correlating with the sinus rate. For example, a typical tidal volume is 500 ml. If the patient breathes 12 breaths per minute then the ventilation volume (minute ventilation) is 6 liters per minute. The device waits until a delta is detected in heart rate of over 30 BPM (e.g. ranging from 60 to 90 BPM) over a one-hour period. Conventional statistical techniques are then used to calculate the correlation coefficient of the minute ventilation vs. the heart rate. As yet another alternative, since $CO_2$ production is correlated with most activity, activity sensors can be used as a surrogate for determining $CO_2$ production. With this technique, the minute ventilation value derived above can be divided by the activity sensor value (scaled appropriately) and then correlated with sinus rate to yield an estimate of VR. This latter technique assumes a functioning sinus node.

Figure 4:
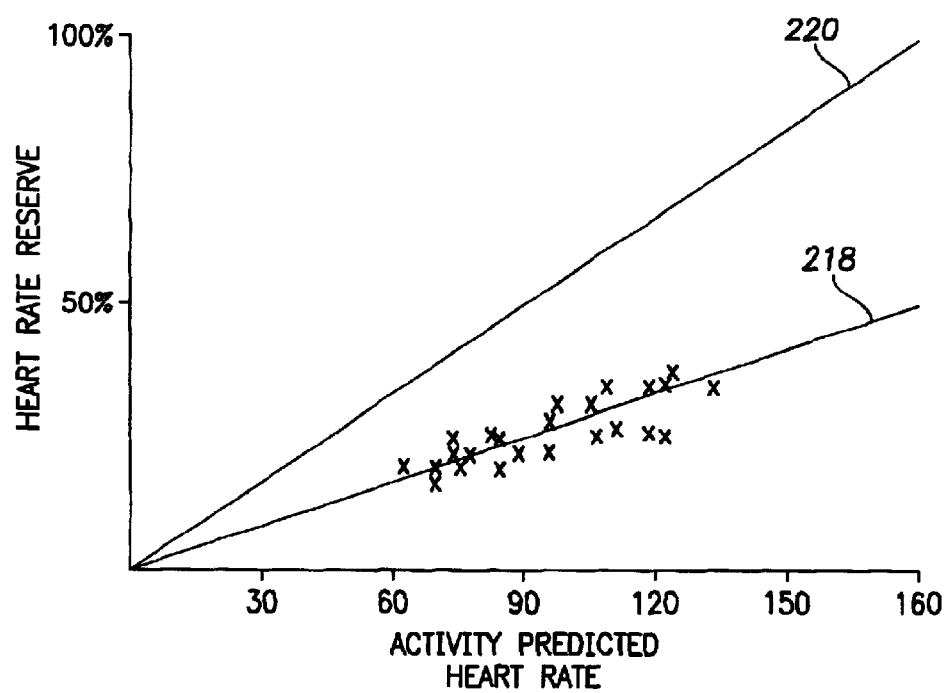
FIG. 4 is a graph illustrating heart rate reserve as a function of predicted heart rate for use by the method of FIG. 3.

Now the calculation of the HRR and ChC values will be described in greater detail. Referring first to FIG. 4, a plot of HRR values as a function of predicted heart rate is shown. Predicted heart rate values are determined (at step 204 of FIG. 3) based on signals from the activity sensor. HRR values are obtained (at step 206 of FIG. 3) by determining the current heart rate of the patient then calculating the following:

$$HRR=(\text{Actual Heart Rate−Rest Heart Rate})/(220-\text{Age−Rest Heart Rate}) \quad \text{Eq. 6}$$

wherein Age is the age of the patient and Rest Heart Rate is a predetermined value, typically around 60 bpm. Steps 204 and 206 of FIG. 3 are performed numerous times each hour to generate numerous HRR vs. predicted heart rate points, which form a scatter plot as shown in FIG. 4. Once an hour, the CHF risk determination unit fits a straight line 218 through the HRR vs. predicted heart rate points using conventional curve-fitting techniques. The slope of line 218 is the ChC value, which is stored for subsequent use in determining the CHF metric. FIG. 4 also shows an ideal response line 220 for a healthy patient. As can be seen, exemplary line 218 has a slope significantly less than the slope of the ideal line, indicating CHF. Note that this technique works only if the patient has a functioning sinus node. Otherwise, the patient will always be paced at the predicted heart rate and the slope of HRR as a function of predicted heart rate (i.e. ChC) will not change with time. Accordingly, for patients without a functioning sinus node, only the VR value determined at step 210 is used in evaluating the risk of mortality. As noted, the VR value is compared with a predetermined VR-based risk threshold value set to 45. If the VR value falls below 45, there is a significant risk of mortality and the warning signal is generated.

Thus, with this technique, a single value for ChC is calculated at any given time for comparison with the predetermined threshold value. In the alternative, separate ChC values are derived within separate ranges of exertion for comparison with separate threshold values. For example, as each HRR value is calculated, the actual heart rate of the patient is compared with predetermined heart rate limits to determine the current level of exertion. The heart rate limits may be, for example:

Daily Activity State: <80 bpm;
Rigorous Activity State: 81–100 bpm; and
Maximum Activity State: >101 bpm.

Then, separate HRR values are calculated within the different levels of exertion:

$HRR_{DAILY\ ACTIVITY}$=(Actual Heart Rate Within Daily Activity Range−Rest Heart Rate)/(220−Age−Rest Heart Rate)   Eq. 7

$HRR_{RIGOROUS}$=(Actual Heart Rate Within Rigorous Activity Range−Rest Heart Rate)/(220−Age−Rest Heart Rate)   Eq. 8

$HRR_{MAXIMUM}$=(Actual Heart Rate Above Maximum Activity Range−Rest Heart Rate)/(220−Age−Rest Heart Rate)   Eq. 9

Thereafter, separate ChC slope values are calculated for the separate levels of exertion yielding: $ChC_{DAILY\ ACTIVITY}$, $ChC_{RIGOROUS}$ and $ChC_{MAXIMUM}$ values, which are compared against separate threshold values for Daily Activity, Rigorous and Maximum activity. If any of the ChC values falls below its corresponding threshold value, the warning signal is generated. Alternatively, the warning signal is only generated if the ChC value for a particular regime, such as the $ChC_{DAILY\ ACTIVITY}$ fails to exceed its corresponding threshold. Also, regardless of whether separate threshold values are employed, the separate ChC values can be at least stored as diagnostic values for subsequent review by the physician.

As noted, for patients without a functioning sinus node, a change in ChC with time cannot be determined because HRR vs. Predicted Heart Rate does not change with time. However, for diagnostic purposes, individual HRR values can be derived from activity sensor values and stored for diagnostic purposes. Initially, activity threshold values are automatically generated by statistically evaluating the frequency of recorded activity sensor values to determine $50^{th}$, $75^{th}$ and $99^{th}$ percentile values. For example, if the activity sensor values range from 0–255, the $50^{th}$ percentile sensor value (i.e. Activity_50%) for a particular patient may be 80, whereas the $75^{th}$ percentile sensor value (i.e. Activity_75%) for the patient may be 125 and the $99^{th}$ percentile sensor value (i.e. Activity_99%) for the patient may be 175. Thereafter, separate HRR values are calculated for the different activity threshold levels:

$HRR_{DAILY\ ACTIVITY}$=(Activity_75%−Activity_50%)/(220−Age−Base Rate)   Eq. 10

$HRR_{RIGOROUS}$=(Activity_95%−Activity_50%)/(220−Age−Base Rate)   Eq. 11

$HRR_{MAXIMUM}$=(Activity_99%−Activity_50%)/(220−Age−Base Rate)   Eq. 12

The separate activity sensor-based HRR values are eventually output to an external programmer device for review by a physician.

What have been described are various techniques performed by an implantable medical device for evaluating the risk of CHF in patients and for generating diagnostic information pertinent thereto. While the invention has been described with reference to particular embodiments, modifications could be made thereto by those skilled in the art without departing from the spirit and scope of the invention.

What is claimed is:

1. In an implantable medical device for implant within a patient, the device having a plurality of sensors and a control unit for processing signals from the sensors, a method performed by the control unit comprising:

receiving signals from the sensors representative of physiological parameters of the patient detected at sub-maximal exertion levels;

estimating the ventilatory response of the patient at maximum exertion based on the signals detected at sub-maximal exertion levels; and controlling at least one function of the device based on the estimated ventilatory response.

wherein the step of receiving signals representative of physiological parameters of the patient includes the step of receiving signals representative of Heart Rate, Arterial Oxygen Saturation, Right Ventricular $O_2$, Stroke Volume, Tidal Volume, and Respiration Rate; and wherein the step of estimating ventilatory response includes the step of calculating $$VR=(\text{Tidal Volume}-\text{Respiratory Rate}) / (\alpha \times (\text{Arterial } O_2 \text{ Saturation} - \text{Right Ventricular } O_2) \times (\text{Heart Rate}) \times (\text{Stroke Volume})).$$

2. The method of claim 1, wherein the coefficient $\alpha$ is about 1.14.

3. In an implantable medical device for implant within a patient, the device having a plurality of sensors and a control unit for processing signals from the sensors, a method performed by the control unit comprising:

receiving signals from the sensors representative of physiological parameters of the patient detected at sub-maximal exertion levels;

estimating the ventilatory response of the patient at maximum exertion base on the signals detected at sub-maximal exertion levels; and controlling at least one function of the device based on the estimated ventilatory resoonse;

wherein the step of receiving signals representative of physiological parameters of the patient includes the step of receiving signals representative of Heart Rate, Arterial Oxygen Saturation, Right Ventricular $O_2$, Tidal Volume, and Respiration Rate; and wherein the step of estimating ventilatory response includes the steps of inputting a Stroke Volume Constant and then calculating $$VR=(\text{Tidal Volume}-\text{Respiratory Rate})/(\alpha \times (\text{Arterial } O_2 \text{ Saturation} - \text{Right Ventricular } O_2) \times (\text{Heart Rate}) \times (\text{Stroke Volume Constant})).$$

4. The method of claim 3 wherein the Stroke Volume Constant is set to about 50 ml.

5. In an implantable medical device for implant within a patient, the device having a plurality of sensors and a control unit for processing signals from the sensors, a method performed by the control unit comprising:

receiving signals from the sensors representative of physiological parameters of the patient detected at sub-maximal exertion levels;

estimating the ventilatory response of the patient at maximum exertion based on the signals detected at sub-maximal exertion levels; and controlling at least one function of the device based on the estimated ventilatory response;

wherein the step of receiving signals representative of physiological parameters of the patient includes the step of receiving signals representative of Heart Rate, Right Ventricular $O_2$, Stroke Volume, Tidal Volume, and Respiration Rate; and wherein the step of estimating ventilatory response includes the steps of inputting an Arterial Oxygen Saturation Constant and then calculating $$VR=(\text{Tidal Volume}-\text{Respiratory Rate}) /(\alpha \times (\text{Arterial } O_2 \text{ Saturation Constant} - \text{Right Ventricular } O_2) \times (\text{Heart Rate}) \times (\text{Stroke Volume})).$$

6. The method of claim 5 wherein the Arterial $O_2$ Saturation Constant is about 0.95.

* * * * *